United States Patent
Noble

(10) Patent No.: US 9,033,907 B2
(45) Date of Patent: May 19, 2015

(54) ADJUSTABLE HINGE

(76) Inventor: Aaron Matthew Noble, Newnan, GA (US)

( * ) Notice: Subject to any disclaimer, the term of this patent is extended or adjusted under 35 U.S.C. 154(b) by 897 days.

(21) Appl. No.: 12/557,210

(22) Filed: Sep. 10, 2009

(65) Prior Publication Data

US 2010/0249683 A1 Sep. 30, 2010

Related U.S. Application Data

(60) Provisional application No. 61/164,647, filed on Mar. 30, 2009.

(51) Int. Cl.
*A61F 5/02* (2006.01)

(52) U.S. Cl.
CPC ............... *A61F 5/028* (2013.01); *Y10T 16/558* (2015.01); *A61F 5/024* (2013.01)

(58) Field of Classification Search
USPC ............ 602/5, 16, 20, 23, 24, 26; 601/23, 33, 601/34; 128/878, 881, 882; 2/225, 226; 411/149–150, 160, 162–163
See application file for complete search history.

(56) References Cited

U.S. PATENT DOCUMENTS

| | | | |
|---|---|---|---|
| 4,599,998 A | 7/1986 | Castillo | |
| 5,180,265 A * | 1/1993 | Wiese | 411/150 |
| 5,292,303 A | 3/1994 | Bastyr et al. | |
| 5,599,288 A * | 2/1997 | Shirley et al. | 602/26 |
| 5,827,208 A | 10/1998 | Mason et al. | |
| 5,873,847 A * | 2/1999 | Bennett et al. | 602/16 |
| 6,039,709 A | 3/2000 | Bzoch | |
| 6,527,733 B1 | 3/2003 | Ceriani et al. | |
| 6,787,160 B2 | 9/2004 | Shacknai et al. | |
| 7,235,058 B2 | 6/2007 | Doty et al. | |
| 7,811,242 B2 * | 10/2010 | Seligman | 602/16 |
| 2007/0078363 A1 | 4/2007 | Kuehnle et al. | |
| 2009/0018476 A1 * | 1/2009 | Cho | 602/16 |

FOREIGN PATENT DOCUMENTS

| | | |
|---|---|---|
| EP | 0016268 A1 | 10/1980 |
| EP | 1138351 A2 | 10/2001 |
| WO | 2007145504 A1 | 12/2007 |
| WO | WO 2007/145504 A1 * | 12/2007 |
| WO | WO 2007145504 A1 * | 12/2007 |

OTHER PUBLICATIONS

Search Report and Written Opinion for International Patent Application No. PCT/US2010/029115; May 11, 2010.

* cited by examiner

*Primary Examiner* — Alireza Nia
*Assistant Examiner* — Ophelia A Hawthorne
(74) *Attorney, Agent, or Firm* — Seyfarth Shaw LLP; Nigamnarayan Acharya

(57) ABSTRACT

An adjustable hinge having a first support arm, a second support arm, and a deformable insert that is between the first support arm and the second support arm.

12 Claims, 8 Drawing Sheets

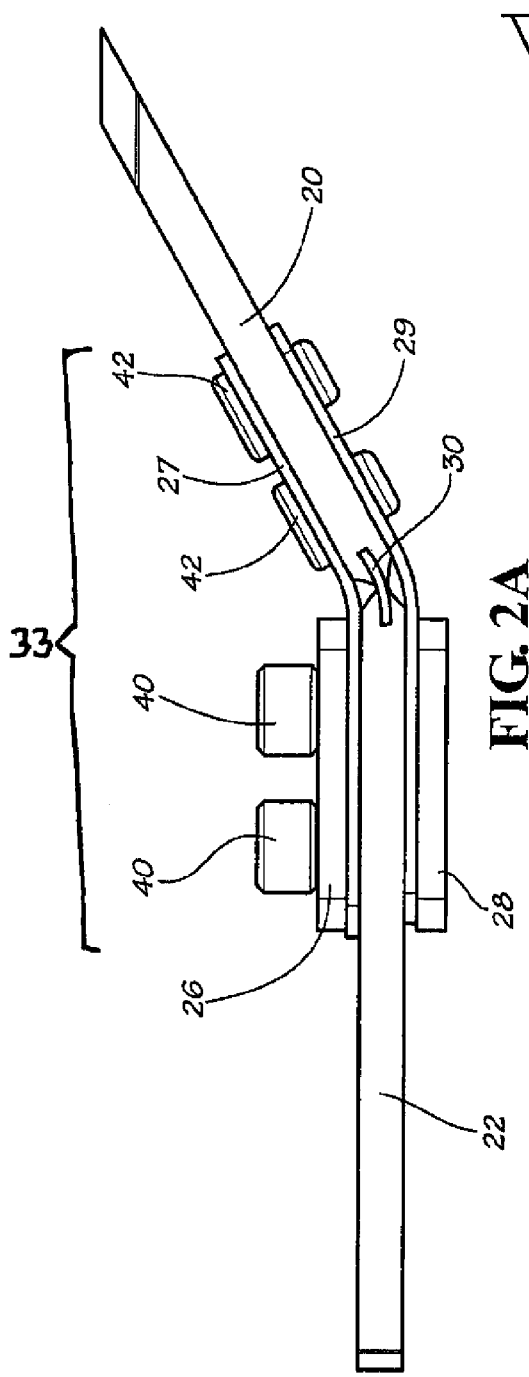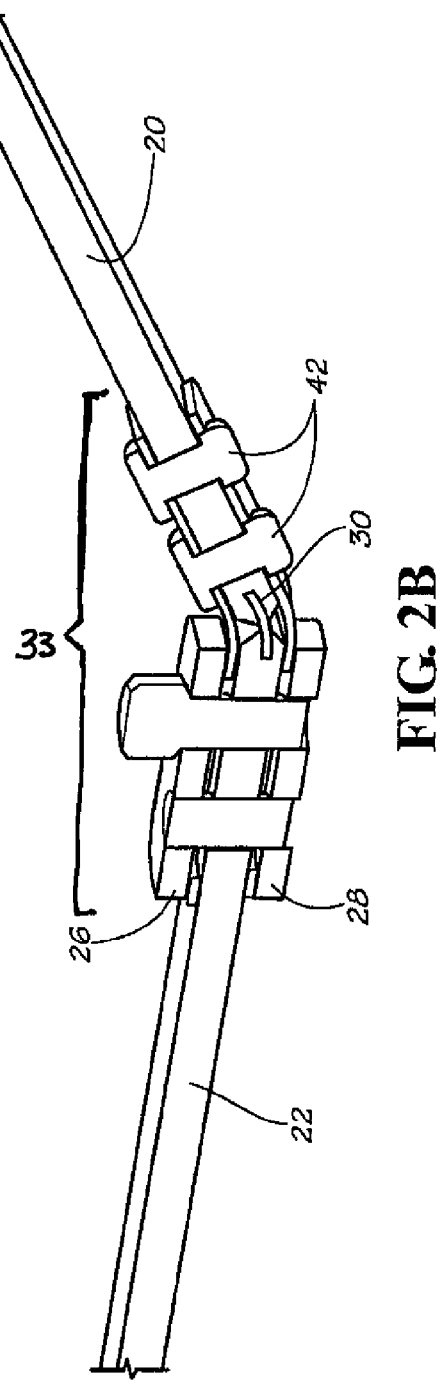

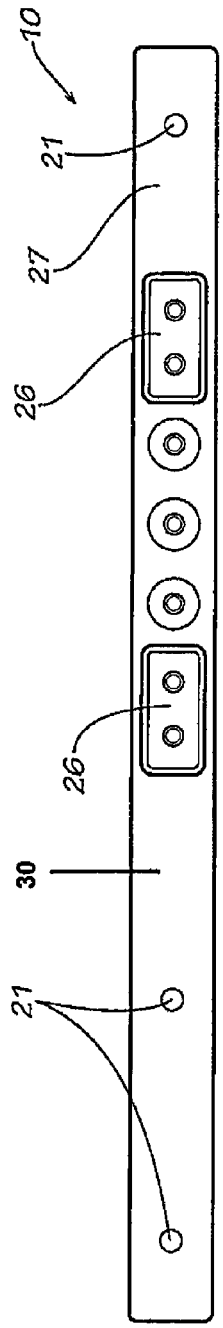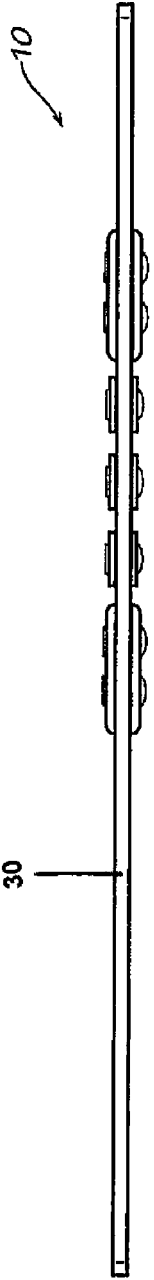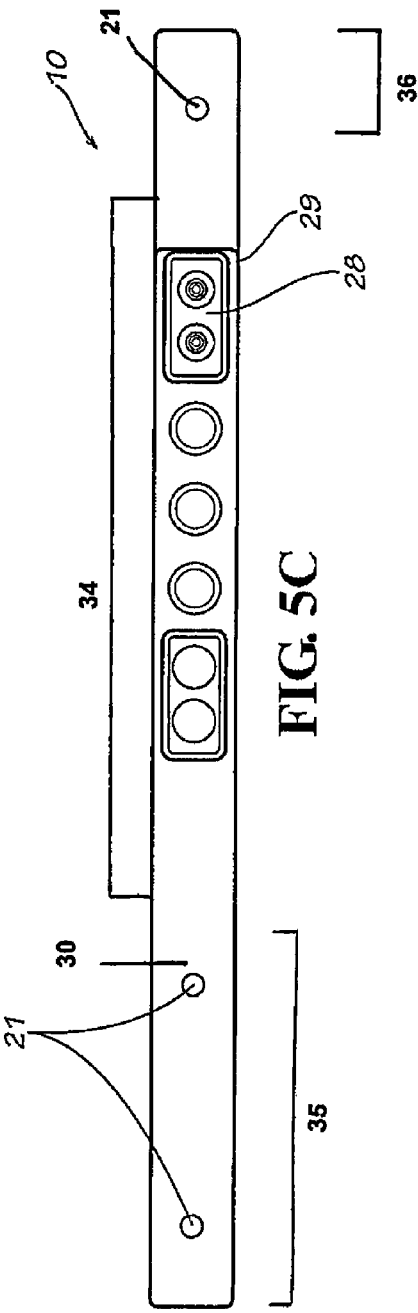
FIG. 5A
FIG. 5B
FIG. 5C

ADJUSTABLE HINGE

PRIOR RELATED APPLICATION DATA

This application claims priority to U.S. Provisional Patent Application Ser. No. 61/164,647 filed Mar. 30, 2009, which is incorporated by reference.

TECHNICAL FIELD

This disclosure relates generally to orthopedic braces and to hinges for braces. This disclosure also relates to an orthopedic brace having a hinge with an adjustable range of movement.

BACKGROUND

Orthopedic braces can be worn to stabilize skeletal joints that have been weakened by injury or other infirmity. Typically, an orthopedic brace has structural components that provide support and stability; and a hinge or joint to dynamically link the structural components, which enables controlled pivotal movement of the structural components during rehabilitation or user activity. In use, a brace can be positioned such that the hinge traverses the skeletal joint being stabilized, while the structural components can be secured to the body at a plurality of engagement faces. Improved therapeutic results may be seen with braces, which are more contoured or tailored to the user.

Accordingly, there is always a need for an improved orthopedic hinge. It is to this need, among others, that this invention is directed.

SUMMARY

This application discloses various exemplary embodiments of an adjustable hinge. In one embodiment, an adjustable hinge comprises a first support arm, a second support arm, and a deformable insert that is between the first support arm and the second support arm. A locking mechanism having a first retention member and a second retention member can also be included to help maintain the position of the arms. The adjustable hinge can be used with an array of braces.

BRIEF DESCRIPTION OF THE DRAWINGS

FIG. 2A is a perspective view of the adjustable hinge of FIG. 1 taken from a side of the adjustable hinge.

FIG. 2B is a side sectional view of the adjustable hinge shown in FIG. 1.

FIG. 5A is a frontal view of another specific embodiment of the adjustable hinge taken from a posterior side of the hinge.

FIG. 5B is a side view of the specific embodiment shown in FIG. 5A.

FIG. 5C is back view of the specific embodiment shown in FIG. 5A.

DETAILED DESCRIPTION

FIGS. 1-8 are intended to illustrate specific embodiments of the adjustable hinge. As can be seen, specific embodiments include an adjustable hinge 10 that can limit the range of movement of the support arms 20, 22 and that can allow positioning arms 20, 22. More particularly, the adjustable hinge 10 can be stopped selectively to allow positioning and repositioning as desired. The adjustable hinge 10 can have stops that resist slippage from their operable position during use of the brace. The adjustable hinge 10 can maintain its rigidity in one plane or more planes of motion.

Figure 1:
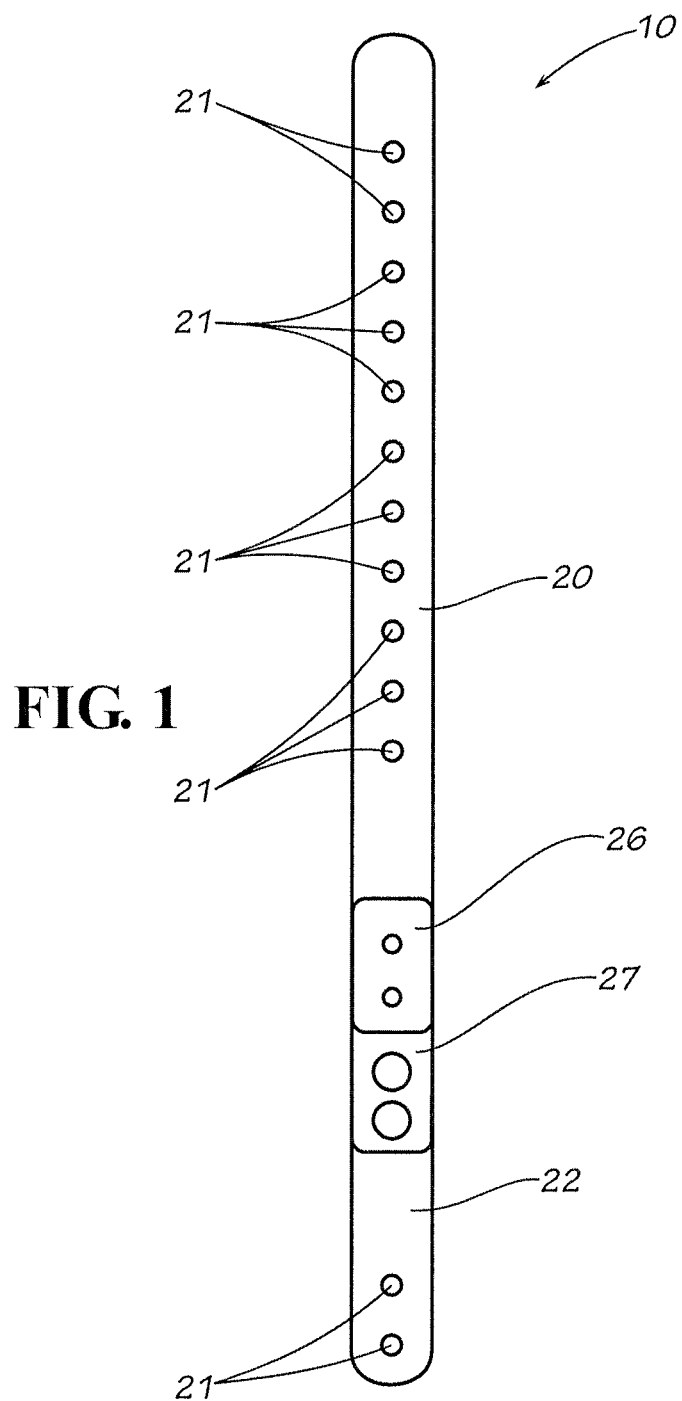
FIG. 1 is a frontal view of a specific embodiment of the adjustable hinge.

As shown in FIG. 1, the adjustable hinge 10 includes a first support arm 20, a second support arm 22, and a deformable insert 30. A frontal view shows that the first support arm 20 and second support arm 22 can be connected through the deformable insert 30 using a washer and a retention member. The first support arm 20 can pivot about the deformable insert 30. In one example, the adjustable hinge 10 includes a first washer 26 situated along the support first arm 22 and a first retention member 27 situated under the first washer 26. The first support arm 20 and the second support arm 22 can have apertures 21 for fastening the adjustable hinge 10 to a bracing structure, such as the brace B shown later in FIG. 7.

As shown in FIGS. 2A and 2B, the first arm 20 and the second arm 22 are held in place by at least one locking mechanism 33, which may be a combination of washers 26, 28, retention members 27, 29 and adjustable fasteners 40. After the adjustable fasteners 40 have been tightened, the retention members 27, 29 and the washers 26, 28 are under pressure, which maintains the shape of the adjustable hinge 10. The first support arm 20 and the second support arm 22 can be connected so that the arms 20, 22 can move at a variety of angles about the deformable insert 30. For example, the first support arm 20 may be moved or angled forward with respect to the second support arm 22. As the first support arm 20 and the second support arm 22 can be connected to separate parts of a structure, it is possible to move the parts relatively independently from each other.

The washers 26, 28, if loose, can move with the movement of either the first arm 20 or the second arm 22. As the ends of washers 26, 28 may be secured along one of the arms 20, 22, the washers 26, 28 can be movable along an unsecured arm. For example, as the first arm 20 is angled or bent, the washers 26, 28 move away from the end of first arm 20 and towards the top of the first arm 20. After the desired position is achieved, the adjustable fasteners 40 can be tightened so to lock the washers 26, 28 in place and to maintain the angle between the first arm 20 and the second arm 22.

As shown, the first washer 26 and the second washer 28 rest on opposite sides of the first support arm 20 and the second support arms 22. Along one of the arms (e.g. the second support arm 22), the respective retention members rest underneath the washers and are secured to a respective arm via an adjustable fastener 40, such as a bolt or flexion pin, which can be inserted through the respective retention member, through the respective arm and ultimately into the respective washer.

Figure 3A:
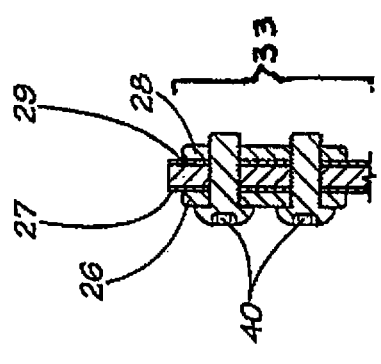
FIG. 3A is a close-up view of an exemplary locking mechanism for use with various specific embodiments of the adjustable hinge.
Figure 3B:
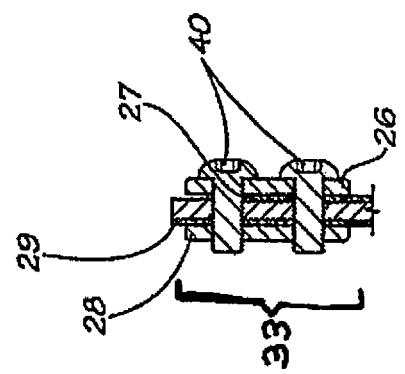
FIG. 3B is a close-up view of another exemplary locking mechanism for use with various specific embodiments of the adjustable hinge.

FIGS. 3A and 3B are close-up views of exemplary locking mechanisms 33 with various specific embodiments. FIG. 3A shows an exemplary locking mechanism 33 in which the bend in the adjustable hinge 10 is held in place using a washer that is held in place by pressure applied from the fastener 40. FIG. 3B shows another exemplary locking mechanism in which the bend in the adjustable hinge is held in place using a washer having a serrated edge that can effectively apply friction to the respective portion of the respective arm 20, 22. To create additional friction, it is contemplated that the surface along the arm shared with the washer 26, 28 can also have serrations.

Figure 4:
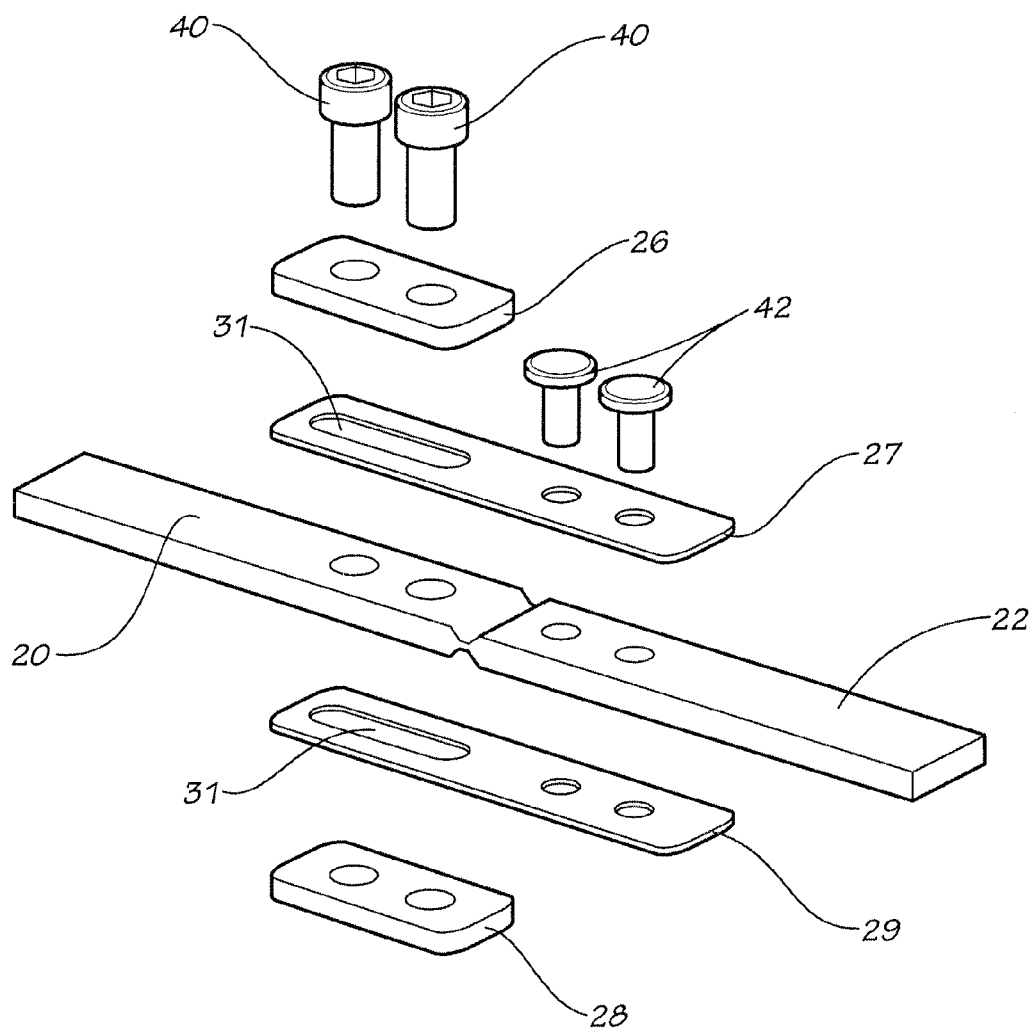
FIG. 4 is an exploded perspective view of the adjustable hinge of FIG. 1 taken from a side of the adjustable hinge.

FIG. 4 shows generally the arrangement in one specific embodiment of the arms 20, 22, the deformable insert 30, the retention members 27, 29, the washers 26, 28, and the fasteners 40. The washers 26, 28 can have an elongated aperture 31 complimentary to the width of the bolt apertures on the first arm 20 with semicircular ends that align to the fastener apertures 42 on the rectangular end of the first arm and contains apertures 42 that align to the complementary rivet apertures on the second arm 22. The washer 26, 28 can have an elongated aperture 31 complimentary to the width of the fastener apertures on the rectangular end of the first arm 22 and contains rivet apertures that align to the complementary rivet apertures on the rear joint element.

As shown in FIGS. 5A, 5B, and 5C, other embodiments can include an adjustable hinge 10 with a continuous structure. The deformable plate insert 30 can have apertures 21 that align to the complementary set of apertures located at the slotted rectangular ends of the forward and rear joint elements. The forward, rear, and continuous joint elements can be made out of various materials, such as but not limited to aluminum (or any other metal or metal alloy), wood, nylon (or any other polymer or polymer combination), or any other sufficiently rigid material, and aluminum has been used in certain examples.

Figure 6A:
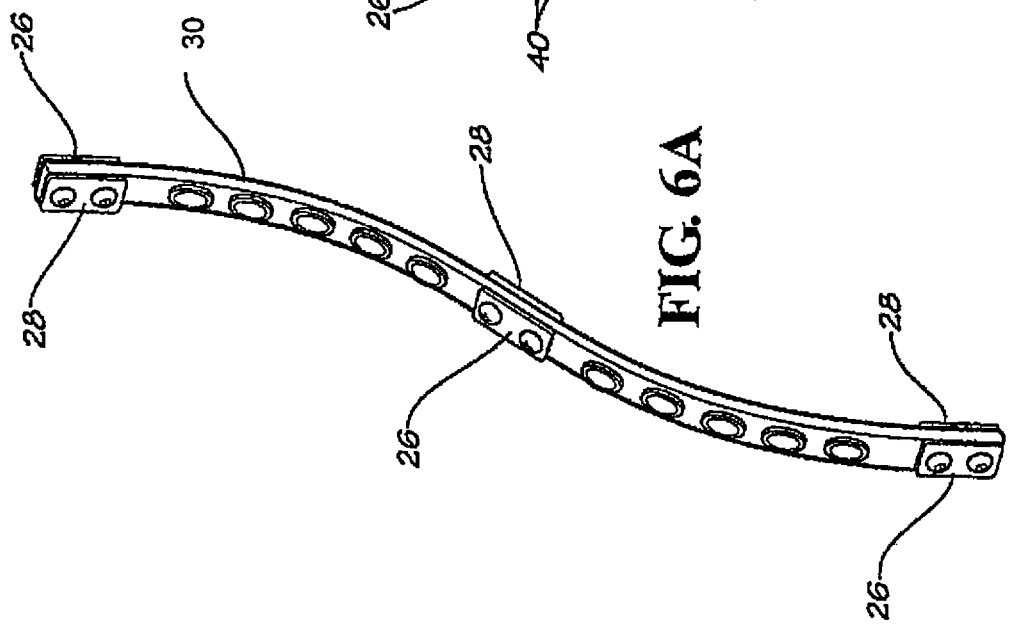
FIG. 6A is a frontal view of another specific embodiment of the adjustable hinge taken from the side of the hinge.

As shown in FIG. 6A, another embodiment can include an adjustable hinge 10 as continuous structure, which comprises a locking mechanism at points along the adjustable hinge 10. In this embodiment, the continuous structure is substantially a deformable material that can be bent to a desired shape. The locking mechanism can help hold the adjustable hinge 10 in its appropriate shape.

Figure 6B:
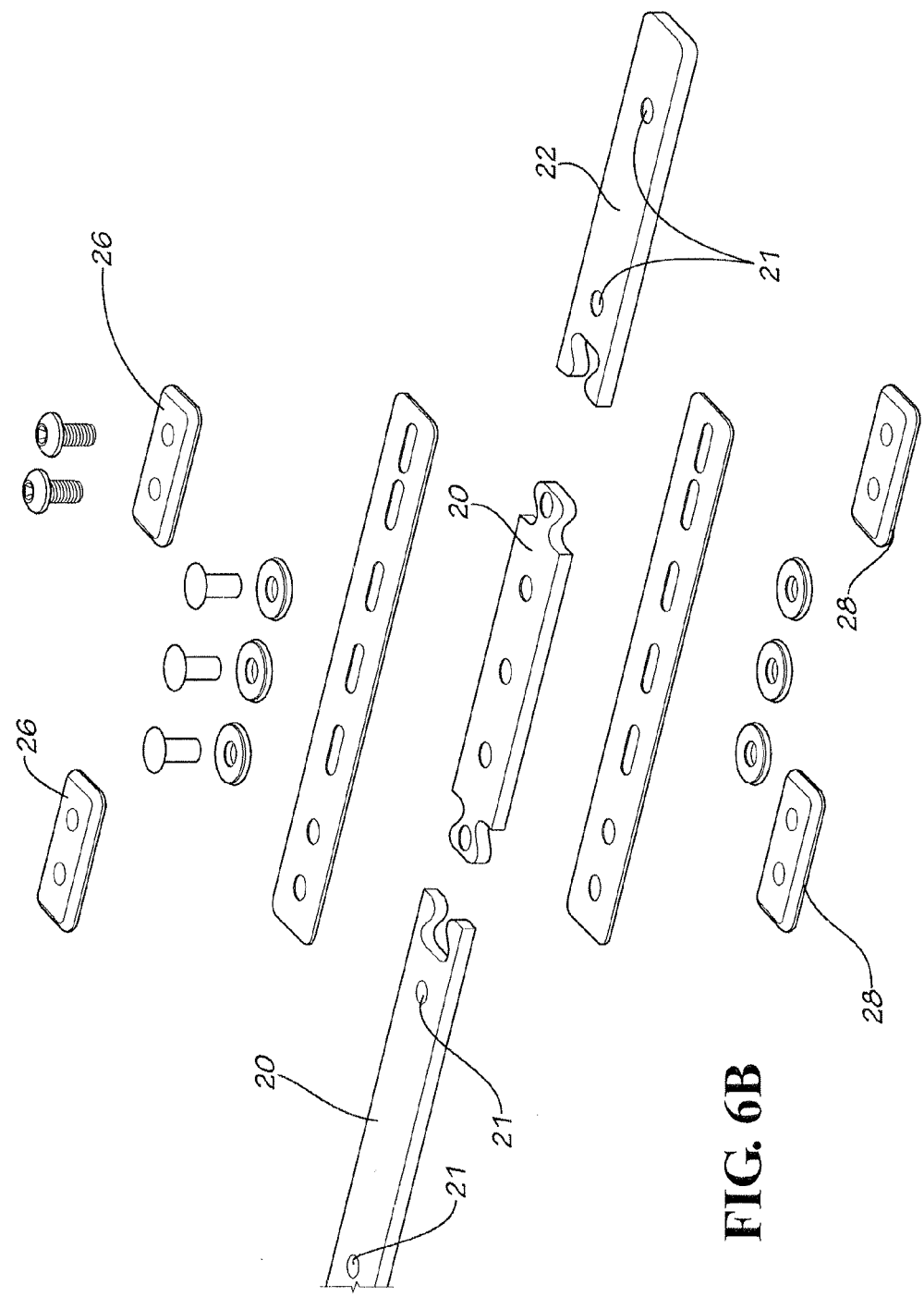
FIG. 6B is an exploded perspective view of another embodiment of the adjustable hinge of the type shown in FIG. 6A.

FIG. 6B is an exploded perspective view of another adjustable hinge of the type shown in FIG. 5 in which the deformable insert in placed between the two arms using a "puzzle" type connection. As shown, the edges of the deformable insert cooperate with the edges of the arms so to interlace. A bond, including an adhesive bond or a metal bond (or other bonds known by those with ordinary skill in the art), may further secure the interlaced portion or arms to the deformable insert. In one example, the adjustable hinge appears as a continuous structure that may be adjusted by a locking mechanism.

Figure 7:
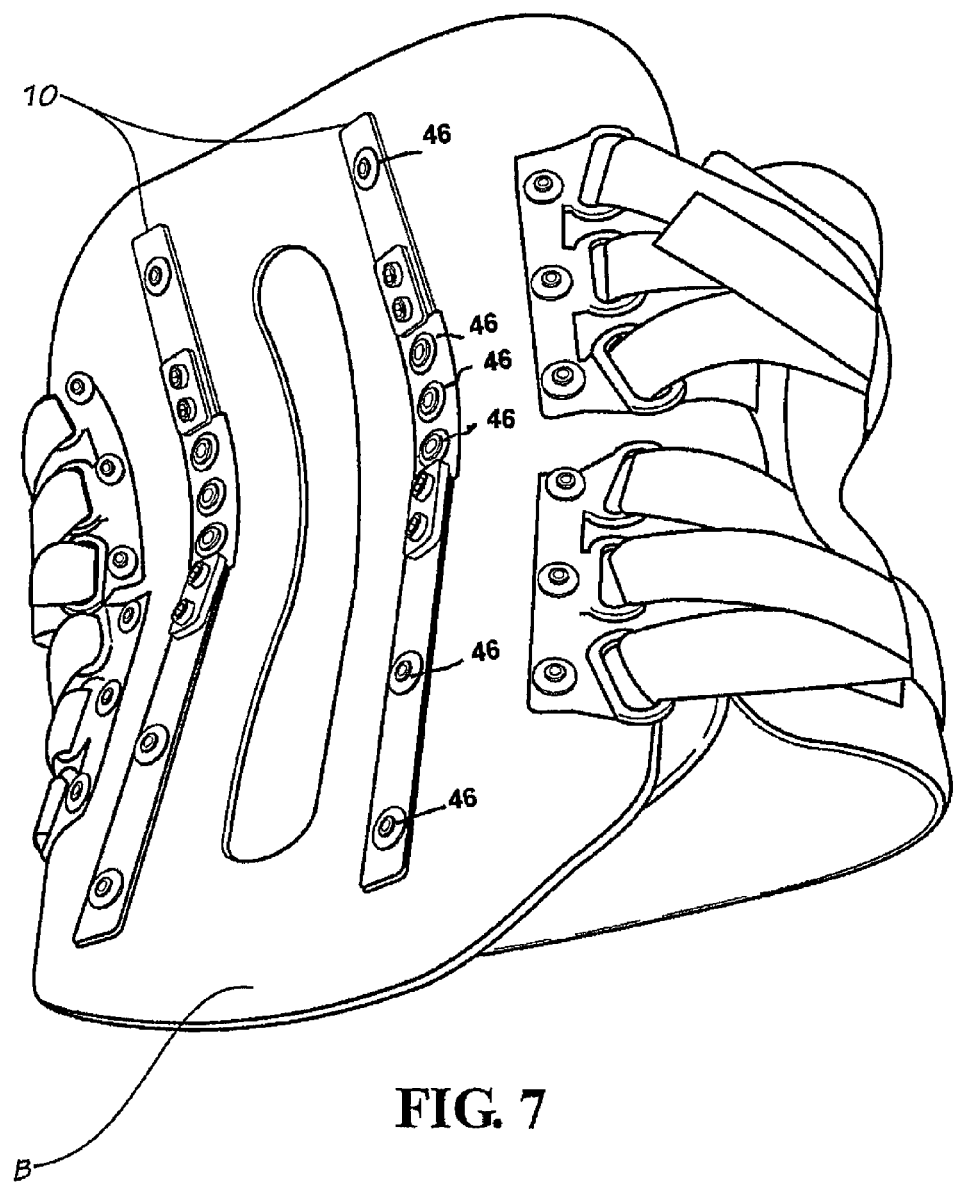
FIG. 7 is a view of a brace incorporating the adjustable hinge shown in FIG. 1.
Figure 8:
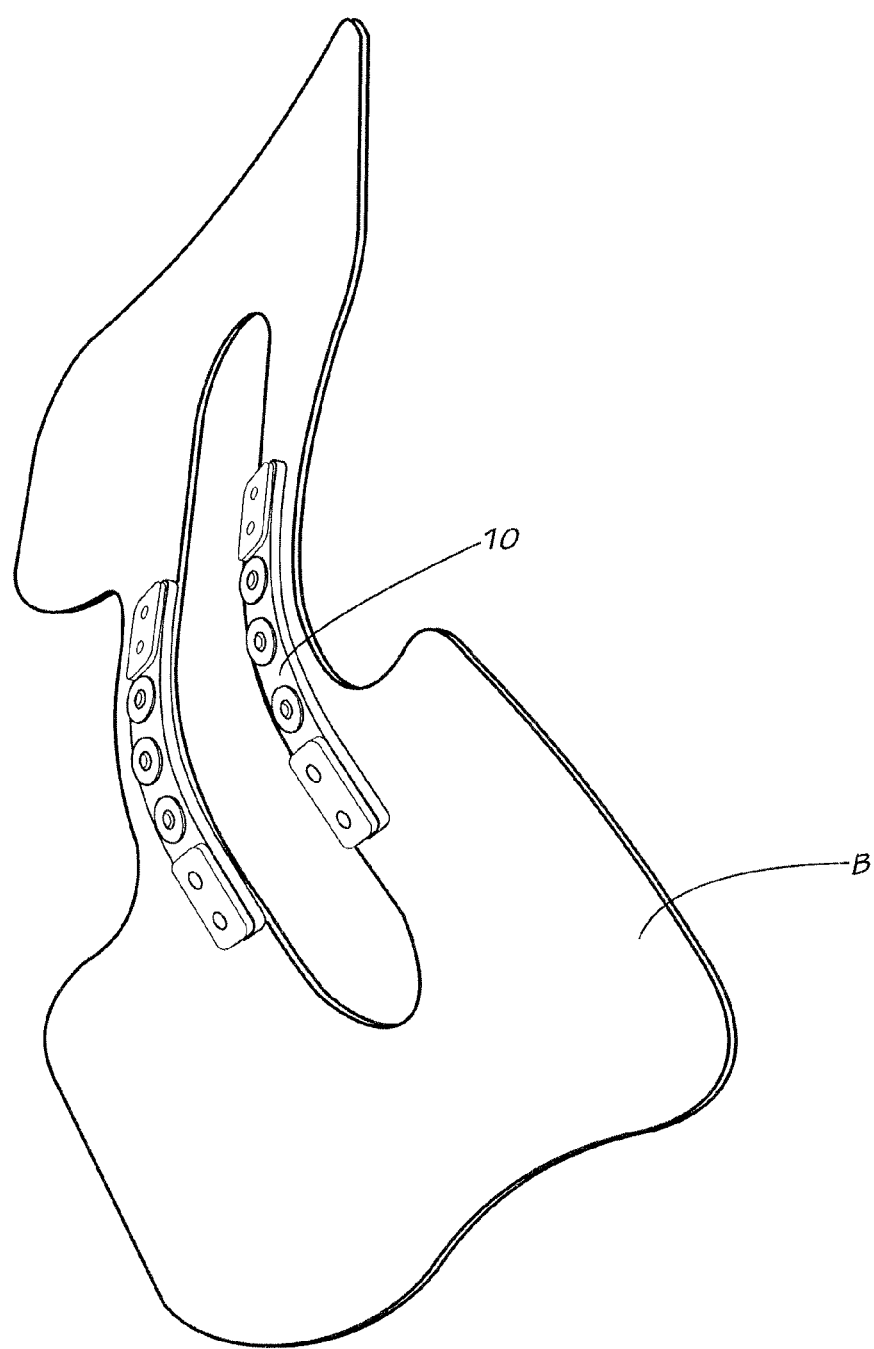
FIG. 8 is a view of a brace incorporating the adjustable hinge shown in FIG. 4.

As shown in FIGS. 7 and 8, the adjustable hinge 10 can be incorporated into structures, such as an orthopedic brace B. The adjustable hinge 10 can have a narrow profile, and can be used in combination other orthopedic joints or hinges. Multiple adjustable hinges may be employed to achieve multiple angles of articulation. The arms 20, 22 can include at least one through-hole 44 for attaching the hinge to a brace B via brace fasteners 46.

As shown in FIG. 7, each through-hole (not shown) cooperates with a brace fastener 46 on the brace to pivotably secure the respective arm 20, 22 to sections of the brace. In this embodiment, the arms 20, 22 are connected to the deformable insert, which is thinner and more flexible than the arms. While the brace fasteners 46 comprise rivets in the illustrated embodiment, those of ordinary skill in the art can appreciate that the brace fasteners 46 can be varied. As can be seen, the adjustable hinge 10 has a broad range of applications in orthopedic bracing as well as other types of bracing.

It is understood that specific embodiments of the adjustable hinge 10 can be adjusted without the use of specialized equipment. In these embodiments, fasteners with ordinary heads and shapes can be used. Using an ordinary tool, e.g. a wrench, the adjustable hinge can lock at a variety of angles.

The materials for manufacturing the adjustable hinge 10 can be obvious to those with ordinary skill in the art. The deformable plate 30 can be made out of various materials, such as but not limited to aluminum (or any other metal or metal alloy), nylon (or any other polymer or polymer combination), or any other sufficiently flexible material. The arms 20, 22 can be made out of various materials, such as but not limited to aluminum (or any other metal or metal alloy), wood, nylon (or any other polymer or polymer combination), or any other sufficiently pliable material, and stainless steel has been used in certain examples. The washers can be made out of various materials, such as but not limited to aluminum (or any other metal or metal alloy), wood, nylon (or any other polymer or polymer combination), or any other sufficiently rigid material, and stainless steel has been used in certain examples.

Fasters, including bolt fasteners and rivets, can be made out of various materials. Adjustable fasteners include those that may be removed or released relatively easy and include, nuts and bolts, rivets, bolts and pins, threaded bolts, or any other type of easily tightened and loosed mechanical fastener and threaded bolts. Secured fasteners include various means, such as but not limited to soldering, epoxy (or any other adhesive or adhesive combination), screws, nuts and bolts, rivets, threaded bolts, bolts and pins, or any other type of sufficiently secure mechanical fastener. One of ordinary skill in the art can select a suitable fastener without undue experimentation.

Specific embodiments of the adjustable hinge can provide users (e.g. orthopedists) the ability to easily achieve an infinite number of fixed angles within a given range of angles. While the specific embodiments are shown with orthothpedic braces, it is understood that the adjustable hinge can be used with an array of structures. For example, the adjustable hinge can be used with vehicle parts (e.g. seats); medical devices (e.g. surgical hand positioning devices, implantable devices and retractors); and tripod components, In such uses, the structures can be adjusted in a variety of angles and planes.

The above detailed description, the drawings, and the examples, are for illustrative purposes only and are not intended to limit the scope and spirit of the invention, and its equivalents, as defined by the appended claims. One skilled in the art will recognize that many variations can be made to the invention disclosed in this specification without departing from the scope and spirit of the invention.

The invention claimed is:

1. An adjustable hinge comprising:
a) a first support arm having a first end;
b) a second support arm having a second end disposed proximal to the first end of the first support arm;
c) a deformable insert between the first end and the second end and continuously connected to the first end and the second end;
d) a locking mechanism along the deformable insert that assists in maintaining the shape of the deformable insert, the locking mechanism including:
a first retention member having a rectangular shape, the first retention member arranged on a first side of the deformable insert and attached immovably to the second support arm and movable to the first support arm; and a second retention member having a rectangular shape, the second retention member arranged on a second side of the deformable insert opposite the first side and attached immovably to the second support arm and movable to the first support arm;

e) a first washer having a rectangular shape, the first washer disposed adjacent the first retention member and attached movably along the first support arm; and f) a second washer having a rectangular shape, the second washer disposed adjacent the second retention member and attached movably along the first support arm.

2. The adjustable hinge as claimed in claim 1, wherein the first support arm comprises a through-hole suitable for securing the first support arm to a brace with a fastener.

3. The adjustable hinge as claimed in claim 1, wherein the first washer is attached movable to the first support arm with an adjustable fastener.

4. The adjustable hinge as claimed in claim 1, wherein the first washer is placed over a first outer surface of the first retention member and along the first support arm, and the second washer is placed over a second outer surface of the second retention member and along the first support arm.

5. The adjustable hinge as claimed in claim 4, wherein an adjustable fastener is released to allow the first and second support arms to bend along the deformable insert.

6. The adjustable hinge as claimed in claim 4, wherein an adjustable fastener is released to allow the first and second support arms to bend about the deformable insert.

7. A method for securing a brace comprising:
a) providing the brace having an adjustable hinge having a first support arm having a first end, a second support arm having a second end proximal to the first end, a deformable insert between the first end and the second end, and a locking mechanism;
b) adjusting the hinge by bending at least one of the first and second support arms about the deformable insert to deform the deformable insert and cause a first retention member and a second retention member of the locking mechanism to move along the first support arm; and
c) securing the shape of the deformable insert by adding tension onto the first and second retention members compressing the first support arm between the first and second retention members.

8. The method as claimed in claim 7, wherein the adjustable hinge is secured in place after adjusting the adjustable the hinge.

9. The adjustable hinge as claimed in claim 7, wherein the first support arm is substantially flat, and the second support arm is substantially flat.

10. An adjustable hinge comprising:
a) a first support arm having a first end;
b) a second support arm having a second end disposed proximal to the first end;
c) a deformable insert between the first end and the second end and continuously coupled to the first and second ends;
d) a locking mechanism along the deformable insert that assists in maintaining the shape of the deformable insert, the locking mechanism including a first retention member and a second retention member arranged on opposite sides of the deformable insert in a layered relationship, the first and second retention members immovably coupled to the second support arm and movably coupled to the first support arm;
e) a first washer disposed adjacent to the first retention member and movable along a first elongated aperture in the first retention member; and
f) a second washer disposed adjacent to the second retention member and movable along a second elongated aperture in the second retention member aligned with the first elongated aperture.

11. The hinge as claimed in claim 10, wherein the first retention member has a rectangular shape; and the second retention member has a rectangular shape.

12. A brace comprising:
a hinge having:
(i) a first support arm secured to one part of the brace, the first support arm having a first end;
(ii) a second support arm secured to another part of the brace, the second support arm having a second end proximal to the first end;
(iii) a deformable insert between the first end and the second end and continuously connected to the first end and the second end;
(iv) a locking mechanism along the deformable insert that assists in maintaining the shape of the deformable insert, the locking mechanism including a first retention member and a second retention member arranged on opposite sides of the deformable insert in a layered relationship, the first and second retention members being immovably attached to the second support arm and movably attached to the first support arm;
(v) a first washer disposed adjacent the first retention member and movable along the first support arm, and
(vi) a second washer disposed adjacent the second retention member and movable along the first support arm.

* * * * *